United States Patent [19]

Schachar

[11] 4,373,218
[45] Feb. 15, 1983

[54] VARIABLE POWER INTRAOCULAR LENS AND METHOD OF IMPLANTING INTO THE POSTERIOR CHAMBER

[76] Inventor: Ronald A. Schachar, 1020 Highway 75 North, Denison, Tex. 75020

[21] Appl. No.: 207,638

[22] Filed: Nov. 17, 1980

[51] Int. Cl.³ .......................... A61F 1/16; A61F 1/24
[52] U.S. Cl. ........................................................ 3/13
[58] Field of Search ..................... 3/13, 1; 128/303 R, 128/305, 276

[56] References Cited

U.S. PATENT DOCUMENTS

| | | |
|---|---|---|
| 2,555,076 | 5/1951 | Crossley ......................... 128/303 R |
| 3,468,602 | 9/1969 | Rosen . |
| 3,473,868 | 10/1969 | Young et al. . |
| 3,525,565 | 8/1970 | O'Neill et al. . |
| 3,533,683 | 10/1970 | Stark et al. . |
| 3,533,684 | 10/1970 | Stark et al. . |
| 3,551,026 | 12/1970 | Heilmeier . |
| 3,583,794 | 6/1971 | Newman . |
| 3,598,479 | 8/1971 | Wright . |
| 3,614,215 | 10/1971 | Mackta . |
| 3,679,295 | 7/1972 | Newman et al. . |
| 3,689,135 | 9/1972 | Young et al. . |
| 3,711,870 | 1/1973 | Deitrick ..................................... 3/13 |
| 3,736,938 | 6/1973 | Evvard et al. ....................... 128/305 |
| 3,803,408 | 4/1974 | Assouline et al. . |
| 3,857,629 | 12/1974 | Freiser . |
| 3,913,148 | 10/1975 | Potthast ..................................... 3/13 |
| 3,951,527 | 4/1976 | Blanz . |
| 3,961,181 | 6/1976 | Golden . |
| 3,984,156 | 10/1976 | Jernigan . |
| 3,991,426 | 11/1976 | Flom et al. ............................... 3/13 |
| 4,002,169 | 1/1977 | Cupler ................................. 128/276 |
| 4,033,349 | 7/1977 | Baehr ............................... 128/303 R |
| 4,037,929 | 7/1977 | Bricot et al. . |
| 4,039,254 | 8/1977 | Harsch . |
| 4,053,953 | 10/1977 | Flom et al. ............................... 3/13 |
| 4,059,348 | 11/1977 | Jernigan . |
| 4,078,856 | 3/1978 | Thompson et al. . |
| 4,180,075 | 12/1979 | Marinoff ............................ 128/305 |
| 4,181,408 | 1/1980 | Senders . |
| 4,190,330 | 2/1980 | Berreman . |
| 4,206,518 | 6/1980 | Jardon et al. ............................. 3/13 |
| 4,251,887 | 2/1981 | Anis .......................................... 3/13 |
| 4,253,199 | 3/1981 | Banko ....................................... 3/13 |

FOREIGN PATENT DOCUMENTS 2525377 12/1976 Fed. Rep. of Germany ............ 3/13

OTHER PUBLICATIONS

*American Journal of Ophthalmology*, vol. 75, No. 4, May, 1973, pp. 755–763, "Four Years' Experience With Binkhorst Lens Implantion".

*Primary Examiner*—Ronald L. Frinks
*Attorney, Agent, or Firm*—Ronald A. Schachar

[57] ABSTRACT

A posterior chamber intraocular lens (34) is provided that can be utilized in a human eye. The posterior chamber intraocular lens (34) includes a fluid-expandable sac (40) for containing a fluid (42). The fluid expandable sac (40) includes a lens portion (36) and a valve portion (38) that extends through the sclera (16) of an eye (10) when the posterior chamber intraocular lens (34) is inserted into the eye (10). In an alternate embodiment, the fluid (42) is a liquid crystal material (52) that is used in combination with an electrode (54) and a microprocessor (56) for changing the index of refraction of the posterior chamber intraocular lens (48) and responds to the desired accommodation.

37 Claims, 5 Drawing Figures

VARIABLE POWER INTRAOCULAR LENS AND METHOD OF IMPLANTING INTO THE POSTERIOR CHAMBER

TECHNICAL FIELD

This invention relates to intraocular lenses. More particularly, this invention relates to posterior chamber intraocular lenses having variable power.

BACKGROUND ART

Intraocular lenses have been heretofore successfully implanted in human eyes. For example, anterior chamber lenses have been implanted directly behind the cornea, but such a lens is sometimes considered undesirable in that it is positioned very close to the cornea and in some cases may result in traumatization of the endothelium. In order to minimize the problems of anterior chamber lenses, various iris-clip and iridocapsular lenses have been developed.

There have been many other designs of intraocular lenses and the latest and most popular intraocular lens involves the use of posterior chamber lenses. The reason for the popularity of the posterior chamber lens is predominantly because many that are skilled in the art believe that breaking or incising the posterior capsule of the lens results in a higher incidence of retinal detachment and cystoid macula edema. These complications appear to be decreased in any type of extracapsular cataract extraction whether it is done in the standard manner or by the procedures of lensectomy or phacoemulsification.

However, one of the present problems with intraocular lenses is that it is necessary to decide on the power of the lens preoperatively. This can be accomplished, for example, by performing an ultrasound scan and/or evaluating the patient's refraction preoperatively and then making a clinical estimate of the proper power of the lens in order to determine proper refraction of the eye.

Accordingly, there is a need for a posterior chamber lens having a variable power of refraction.

DISCLOSURE OF THE INVENTION

In accordance with the present invention, a posterior chamber intraocular lens for a human eye is provided that includes a fluid-expandable sac that is constructed of a flexible transparent material for containing fluid. The sac is dimensioned for occupying the posterior chamber of an eye in place of the natural lens and contains a fluid when implanted in the posterior chamber of an eye for providing the desired correction, the fluid forming the interior portion of the posterior chamber intraocular lens of the present invention. The sac which forms the exterior portion of the intraocular lens further includes a neck portion that serves as a valve and extends through the sclera of an eye when inserted therein. The valve allows fluid contained in the sac to be withdrawn or replaced to change the index of refraction of the lens, and/or, change the thickness of the lens and thereby change the power of the lens.

In accordance with the surgical procedure provided, the posterior chamber intraocular lens of the present invention is implanted into the eye by inserting a needle through the sclera of the eye and into the posterior chamber. Thereafter, the fluid-expandable sac, constructed of a flexible transparent material is inserted through the needle in a collapsed condition and into the posterior chamber. A fluid is then instilled into the sac thereby expanding it and isolating the vitreous face from the natural lens. Thus, the insertion and expansion of the sac dissects the attachment of the vitreous face from the posterior natural lens capsule. A pressure relief aperture is formed in the cornea of the eye so that pressure produced on the interior portion of the eye as fluid is instilled into the sac is relieved. The natural lens is then extracted from the eye, and may be removed through the pressure relief aperture, by any suitable manner known to those skilled in the art, such as by cryoextraction, extracapsular extraction or phacoemulsification.

In accordance with another embodiment of the posterior chamber intraocular lens of the present invention, the fluid-expandable sac is filled with a liquid crystal material. The accommodation of the eye is monitored and to provide an input signal to a microprocessor that is capable of producing an output voltage proportional to the desired accommodation. The output voltage is transmitted to and applied across the liquid crystal material contained in the sac for providing an index of refraction that is required to achieve the power necessary for the desired accommodation.

DESCRIPTION OF THE DRAWINGS

The present invention can be more completely understood by reference to the following detailed description taken in conjunction with the accompanying drawings in which.

DETAILED DESCRIPTION

In accordance with the present invention, a posterior chamber intraocular lens together with a surgical method for the implantation thereof in a human eye is provided. Unlike previous intraocular lenses, the posterior chamber intraocular lens of the present invention is a nonrigid lens that permits the corrective power of the lens to be changed after implantation thereof into an eye.

Figure 1:
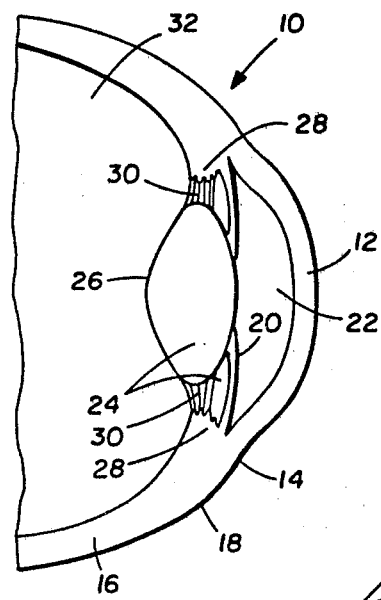
FIG. 1 is a horizontal section through a human eyeball partially broken away.

Referring to the figures generally, and particularly to FIG. 1, there is depicted a horizontal cross section of a human eye, partially broken away and generally referred to by reference numeral 10. Eye 10 includes a cornea 12, limbus 14, a sclera 16, conjunctiva 18, an iris 20, an anterior chamber 22, a posterior chamber 24, a natural lens 26, ciliary body 28, suspensory ligaments 30 and a vitreous chamber 32. The function and interrelationship of these components of the eye are well known and for that reason a detailed explanation of each component is not provided herein.

Figure 3:
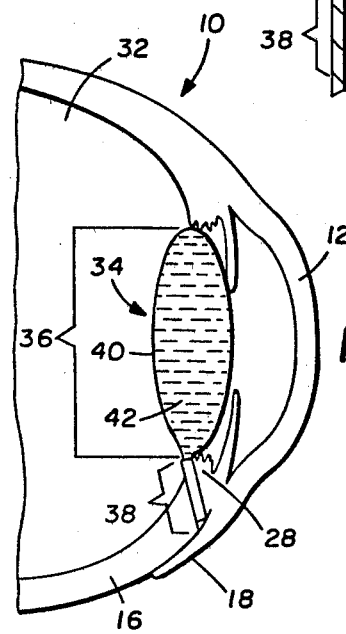
FIG. 3 is a horizontal sectional view of a human eyeball partially broken away showing the posterior chamber intraocular lens implanted in the eye.

A posterior chamber intraocular lens 34 in accordance with the present invention is shown in position in eye 10 in FIG. 3. Posterior chamber intraocular lens 34 includes a lens portion 36 and a valve portion 38. Lens portion 36 preferably occupies the entire posterior chamber taking the place of natural lens 26. Valve portion 38 extends through sclera 16, generally about 2.5 millimeters posterior to limbus 14 of eye 10. The exterior of posterior chamber intraocular lens 34 is a fluid-expandable sac 40 that is constructed of a transparent material compatible with the eye. For example, fluid-expandable sac 40 may be constructed of polypropylene, polyethylene or silicone. Lens portion 36 of fluid-expandable sac 40 is preferably a biconvex shape, as depicted in FIG. 3, when filled with fluid. Alternatively, lens portion 36 of fluid-expandable sac 40 can be a plano-convex shape or any other desired shape. Preferably, lens portion 36 of fluid-expandable sac 40 has a diameter of approximately 13.5 millimeters when the desired amount of fluid is instilled therein so that the peripheral portions of fluid-expandable sac 40 contact ciliary body 28, or may be smaller and fit within the capsule of the lens following an extracapsular cataract extraction.

As shown in FIG. 3, fluid-expandable sac 40 contains a fluid 42 for providing the desired index of refraction for posterior chamber intraocular lens 34. Fluid 42 may be either a gas or a liquid. Preferably fluid 42 will be a liquid since generally the desired index of refraction of lens portion 36 is more easily attainable, since liquids have a greater range of indices of refraction than various gases. Alternatively, the sac may be made so that the walls have optical power and the total optical power of the intraocular lens is altered by varying the distance between the walls of the sac by filling the sac with different amounts of fluid. For example, fluid 42 may be an aqueous saline solution. Alternatively, fluid 42 may comprise a liquid having a higher index of refraction than water, such as an oil, including silicone oil. However, the use of such a material should be carefully evaluated prior to use in a human eye since leakage of some materials from fluid-expandable sac 40 could be deleterious to eye 10.

Thus, fluid-expandable sac 40 isolates posterior chamber 24 from the anterior chamber 22. This facilitates removal of the natural lens as will be hereinafter described. Further, fluid-expandable sac 40 prevents any intrusion into vitreous chamber 32 and maintains the normal vitreous volume without disturbance of the relationship of vitreous chamber 32 to the macula (not shown).

Figure 2:
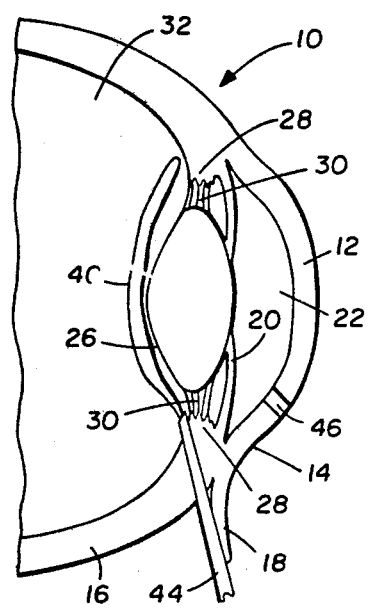
FIG. 2 is a horizontal section through a human eyeball partially broken away illustrating the insertion of a needle through the sclera and into the posterior chamber of the eye.

Referring to FIG. 2, there is illustrated posterior chamber intraocular lens 34 of the present invention being inserted into eye 10. Natural lens 26, illustrated in FIG. 2, generally has some type of physical damage, such as a cataract. This necessitates removal of natural lens 26 which is replaced by posterior chamber intraocular lens 34 of the present invention. Fluid-expandable sac 40 of posterior chamber intraocular lens 34 is placed in posterior chamber 24 of eye 10 in accordance with the following procedure. A peritomy of conjunctiva 18 is performed so that a portion of sclera 16, generally about 2.5 millimeters posterior to limbus 14, is uncovered. Thereafter, an insertion member, such as a hollow needle 44, for example, is inserted into and through that portion of sclera 16 that has been uncovered by the peritomy of conjunctiva 18, preferably in the area of the pars plana. Hollow needle 44 is then inserted into vitreous chamber 32. Preferably, hollow needle 44 generally protrudes between about 1 and 2 millimeters into posterior chamber 24. Hollow needle 44 is dimensioned to permit insertion of fluid-expandable sac 40 into the hollow portion thereof. Collapsed fluid-expandable sac 40 of posterior chamber intraocular lens 34 is then inserted into and through hollow needle 44. Fluid-expandable sac 40 is then expanded with a fluid 42 causing fluid-expandable sac 40 to spread out and fill posterior chamber 24 to isolate the vitreous from natural lens 26. In this manner, the vitreous face of vitreous chamber 32 is dissected from the posterior lens capsule of natural lens 26 by fluid-expandable sac 40. Prior to instilling fluid 42 into fluid-expandable sac 40, a pressure relief aperture 46 is formed in cornea 12. Since instilling fluid 42 into fluid expandable sac 40 increases the interior pressure of eye 10, which could cause deleterious effects, this pressure is relieved by allowing fluid to exit through pressure relief aperture 46. Pressure relief aperture 46 can be formed before hollow needle is inserted through sclera 16.

Figure 4:
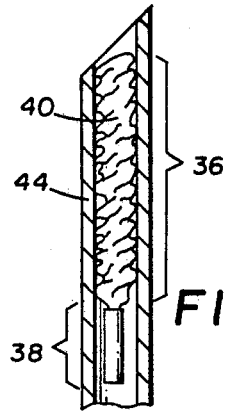
FIG. 4 is a sectional view of a needle, partially broken away, utilized in implanting the intraocular lens of the present invention illustrating a collapsed intraocular lens in accordance with the invention being transported through the needle.

FIG. 4 illustrates fluid-expandable sac 40 being transported through hollow needle 44 in a collapsed state. Fluid pressure can be utilized to force fluid-expandable sac 40 through hollow needle 44 or an instrument, such as a rod, dimensioned to be inserted within hollow needle 44, can be used for this purpose. When fluid-expandable sac 40 is filled with fluid 42 with natural lens 26 removed, posterior chamber intraocular lens 34 occupies posterior chamber 24 as shown in FIG. 3. Preferably, posterior chamber intraocular lens 34 occupies the entire volume of posterior chamber 24. The peripheral portions of fluid-expandable sac 40 can be ribbed or can incorporate small pins (not shown) so that posterior chamber intraocular lens 34 is restrained from movement within posterior chamber 24 of eye 10.

After posterior chamber intraocular lens 34 has been inserted in position in posterior chamber 24 such that the vitreous face of vitreous chamber 32 is separated from natural lens 26, natural lens 26 is then removed. Natural lens 26 can be removed by any manner known to those skilled in the art, such as lensectomy, phacoemulsification, cryoextraction, or extracapsular extraction. Further, entire natural lens 26 may be removed including all of, portions of or none of suspensory ligaments 30. Alternatively, the sac of natural lens 26 can remain with only the crystalline portion of lens 26 being removed. In an alternate embodiment (not shown), fluid-expandable sac 40 can be placed within the sac of natural lens 26 after the crystalline portion thereof is removed. The removed portions of natural lens 26 can be removed through pressure relief aperture 46, if desired.

As shown in FIG. 3, valve portion 38 of fluid-expandable sac 40 forming the exterior of posterior chamber intraocular lens 34, extends through sclera 16. This has the effect of maintaining posterior chamber intraocular lens 34 in a predetermined relation with respect to eye 10. The aperture formed in sclera 16 by hollow needle 44 is closed leaving valve portion 38 therein. Preferably, valve portion 38 protrudes slightly from sclera 16 and is covered with conjunctiva 18 after injection of fluid 42. Thus, it is a relatively simple procedure if it is desired to change the index of refraction of posterior chamber intraocular lens 34, since it is necessary only to add or withdraw fluid 42 from lens 34 or replace fluid 42 with another type of fluid having a different index of refraction.

Figure 5:
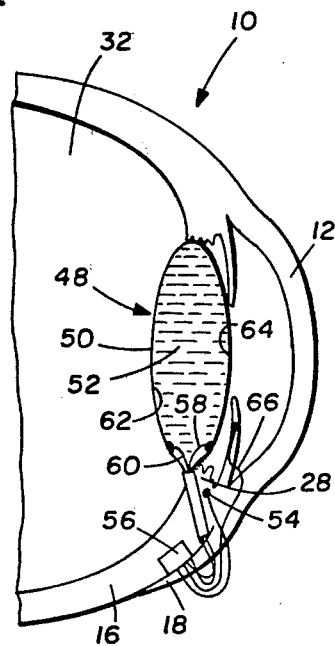
FIG. 5 is a horizontal sectional view of a human eyeball partially broken away showing an alternate embodiment of the posterior chamber intraocular lens of the present invention.

In accordance with another embodiment of the present invention, a posterior chamber intraocular lens 48 is provided utilizing a fluid-expandable sac 50 similar to fluid-expandable sac 40, with fluid-expandable sac 50 being filled with a liquid crystal material 52, as shown in FIG. 5. Posterior chamber intraocular lens 48 is responsive to achieving a desired accommodation by altering the index of refraction of liquid crystal material 52. This can be accomplished in a number of ways which are hereinafter described. For example, the accommodation of the eye can be monitored by measuring the electrical potential generated by ciliary body 28. An electrode 54 is located in ciliary body 28, as shown in FIG. 5, which provides an input signal, that is proportional to the desired accommodation, to a microprocessor 56, which can be implanted into sclera 16 of eye 10 as shown in FIG. 5, or into any other suitable location. A suitable power source is provided for microprocessor 56 and could also be implanted (not shown). Microprocessor 56 may comprise, for example, Model 8080 manufactured and sold by Intel Corporation. Microprocessor processor 56 is programmable in a manner well known to those skilled in the art to provide a corresponding output depending on the relative intensity sensed by electrode 54 which is proportional to the accommodation of the eye. By monitoring the electrical potential generated by ciliary body 28, the refractive power of the intraocular lens can be controlled. Alternatively, an electrical signal proportional to the location of the eyes can be obtained by implanting electrodes in the rectus medialis (not shown) of eye 10. Microprocessor 56 is utilized for producing a voltage output for providing a voltage potential across liquid crystal material 52 contained within fluid-expandable sac 50 to provide the index of refraction that is required to obtain the desired accommodation based upon the relative position of the eyes. The voltage output of microprocessor 56 is transmitted through electrical wires 58 and 60. Electrical wires 58 and 60 connect to electrodes 62 and 64, respectively for applying a voltage potential across liquid crystal material 52. Electrodes 62 and 64 can be a thin transparent material forming a coating on the interior of fluid-expandable sac. For example, a thin coating of tin oxide and indium oxide can be used for electrodes 62 and 64.

In accordance with another embodiment of the present invention, liquid crystal material 52 may comprise a material that darkens on an increase in the voltage potential supplied across such a liquid crystal material. A small photo electric cell (not shown) is mounted in the conjunctiva of the eye for monitoring the ambient light for automatically altering the optical density of the liquid crystal material.

In accordance with another embodiment of the present invention, instead of using a photo electric cell to monitor the ambient light, a small electrode 66 can be placed in the iris of the eye and the size of the pupil or contraction of the iris which occurs under a particular lighting condition can be used to monitor the potential generated so that the intraocular lens would then become darkened when the pupil started to contract with increasing light. It is well known that the pupil contracts under two circumstances, when there is increased light and when one is reading or looking at a close object. During the reading phase the ciliary body also contracts in order to produce normal accommodation and electrode 54 is provided for sensing ciliary muscle in order to alter the refractive index of the liquid crystal for the reading and simultaneous monitor the iris contraction. This allows a determination to be made when both the iris and ciliary muscle contract to therefore prevent the lens from darkening when reading. However, when the eye looks at a bright room it is not reading, or looking at close objects, the pupil would be small but the ciliary body would not contract and therefore there would be an impulse only from the iris so that the lens would then be darkened. By proper choosing the type of liquid crystal material, it would be possible to control both optical density and index of refraction of posterior chamber intraocular lens 48. For example, by utilizing a liquid crystal material that darkens under an applied voltage between $V_o$ and $V_1$, and changes its index of refraction under an applied voltage between $V_2$ and $V_3$, where the range of $V_0$ to $V_1$ is exclusive of the range of $V_2$ to $V_3$, both the index of refraction and optical density of posterior chamber intraocular lens 48 can be controlled utilizing electrodes 54 and 66.

In another embodiment, the fluid-expandable sac may contain a material which, in direct response to increased light, becomes optically denser. With this embodiment, it would not be necessary to incorporate electrodes to monitor microcontractions and relaxation if the material would automatically change its optical density is a direct response to the lighting condition.

While the invention has been described with respect to preferred embodiments, it is to be understood that the invention is capable of numerous modifications, rearrangements and changes that are within the scope of the invention as defined by the appended claims.

I claim:

1. A posterior chamber intraocular lens for an eye comprising:
    a fluid-expandable sac constructed of flexible, transparent material for containing fluid and dimensioned for occupying the posterior chamber of the eye when expanded with fluid in place of at least a portion of the natural lens; and
    valve means connected to said sac for extending through the sclera of the eye for selectively varying the optical characteristics of the fluid within said sac in order to vary the optical characteristics of the wearer's eye while said sac is in the wearer's eye.

2. The posterior chamber intraocular lens as recited in claim 1 wherein the shape of said sac when expanded with fluid is biconvex.

3. The posterior chamber intraocular lens as recited in claim 1 wherein said fluid-expandable sac is dimensioned to occupy essentially the entire posterior chamber of the eye when expanded with fluid.

4. The posterior chamber lens as recited in claim 1 wherein said fluid-expandable sac is filled with fluid of a predetermined index of refraction for providing a lens having a desired power.

5. The lens as recited in claim 4 wherein said fluid is a gas.

6. The lens as recited in claim 4 wherein said fluid is an aqueous solution.

7. The lens as recited in claim 4 wherein said fluid is an oil.

8. The lens as recited in claim 7 wherein said fluid is silicone oil.

9. The lens as recited in claim 4 wherein said fluid is water.

10. The lens as recited in claim 4 wherein said fluid is nonreactive with the eye.

11. The lens as recited in claim 1 wherein said fluid-expandable sac can be transported through a needle when collapsed.

12. The lens as recited in claim 1 further comprising means for maintaining said sac in a fixed position in the posterior chamber of the eye.

13. The lens as recited in claim 12 wherein said means for maintaining said sac in a fixed position includes projections on the exterior of said sac.

14. The lens as recited in claim 13 wherein said projections are pin-like.

15. The lens as recited in claim 13 wherein said projections are rib-like.

16. The lens as recited in claim 1 wherein said sac is constructed of materials selected from the group consisting of polypropylene, polyethylene and silicone.

17. The lens as recited in claim 1 wherein said sac is dimensioned when expanded to occupy the interior portion of the natural lens sac.

18. A posterior chamber intraocular lens for an eye comprising:
(a) a fluid-expandable sac constructed of a transparent flexible material for containing fluid and dimensioned for occupying the posterior chamber of an eye;
(b) liquid crystal material contained within said sac having an index of refraction that is variable by an applied voltage;
(c) means for producing an input signal proportional to the accommodation of the eye; and
(d) microprocessor means electrically coupled to said liquid crystal material and responsive to an input signal for producing an output signal for controlling the index of refraction of said liquid crystal material for achieving the desired accommodation.

19. The lens as recited in claim 18 wherein said means for producing an input signal includes a sensor for monitoring the position of the eyes.

20. The lens as recited in claim 18 wherein said sensor monitors the position of the eyes by measuring the electric potential generated by the rectus medialis.

21. The lens as recited in claim 18 wherein said means for producing an input signal includes an electrode for monitoring the electrical potential generated by contractions and relaxations of the ciliary body of the eye.

22. The lens as recited in claim 21 wherein the optical density of said liquid crystal is variable by an applied voltage potential.

23. A method for removing a natural lens from an eye and for implanting into the eye a posterior chamber intraocular lens comprising:
(a) inserting an insertion member through the sclera of the eye and into the posterior chamber;
(b) inserting a collapsible, fluid-expandable sac constructed of flexible transparent material through said member and into the posterior chamber; and
(c) instilling a fluid into said sac for filling said sac in order to provide an artificial lens.

24. The method of claim 23 and further comprising forming an aperture in the cornea of the eye for relieving pressure produced on the interior portion of the eye as fluid is instilled into the sac.

25. The method as recited in claim 23 wherein at least a portion of the natural lens is removed after said fluid-expandable sac is inserted into the posterior chamber.

26. The method as recited in claim 25 wherein the lens is removed by phacoemulsification.

27. The method as recited in claim 25 wherein the lens is removed by cryoextraction.

28. The method as recited in claim 25 wherein the lens is removed by an extracapsular procedure.

29. The method as recited in claim 23 further comprising sealing said sac having fluid contained therein, said sac functioning as a posterior intraocular lens.

30. The method as recited in claim 23 wherein said fluid-expandable sac is inserted into the natural lens sac.

31. The method as recited in claim 25 wherein the entire natural lens is removed.

32. The method as recited in claim 25 wherein only the crystalline material of the natural lens is removed.

33. The method as recited in claim 32 wherein the intraocular lens is posterior to the natural lens sac.

34. The method as recited in claim 23 wherein said fluid is a liquid crystal material.

35. The method as recited in claim 34 wherein said fluid-expandable sac has electrodes on interior portions thereof.

36. The method as recited in claim 35 further comprising:
(a) implanting an electrode in the ciliary muscle of the eye;
(b) connecting said electrode to the input of a microprocessor; and
(c) connecting the output of said microprocessor to the electrodes located on the interior of said fluid-expandable sac.

37. The method as recited in claim 23 wherein said insertion member is a hollow needle that is inserted about 2.5 millimeters posterior to the limbus of the eye.

* * * * *